(12) United States Patent
Kang et al.

(10) Patent No.: US 6,338,846 B1
(45) Date of Patent: Jan. 15, 2002

(54) RECOMBINANT BACULOVIRUS, CONSTRUCTION METHOD THEREOF AND INSECT PESTICIDAL COMPOSITION CONTAINING THE SAME

(76) Inventors: Seok-Kwon Kang, 104-801, Hyundai Apt, Maetan-dong, Paldal-ku, Suwon-city, Kyunggi-do 442-370; Yeon-Ho Je, 45-71, Seodoon-dong, Kwonsun-ku; Byung-Rae Jin, 205, Kyokwan Apt, Seodoon-dong, Kwonsun-ku, both of Suwon-city, Kyunggi-do 441-100; Hyun-Woo Park, 18-81, Shibum Apt, Yoido-dong, Youngdungpo-ku, Seoul 150-010; Jong-Yul Roh, 28/4, 1000-3, Sadang-4-dong, Tongjak-ku, Seoul 156-094; Jin-Hee Chang, 21-1206, Hanyang Apt, Songpa-dong, Songpa-ku, Seoul 138-170, all of (KR)

( * ) Notice: Subject to any disclaimer, the term of this patent is extended or adjusted under 35 U.S.C. 154(b) by 0 days.

(21) Appl. No.: 09/187,164
(22) Filed: Nov. 6, 1998

(30) Foreign Application Priority Data

Apr. 3, 1998 (KR) .............................. 98-11914

(51) Int. Cl.[7] .......................... A01N 63/00; C12N 7/01; C12N 15/866
(52) U.S. Cl. ................ 424/93.2; 435/320.1; 435/235.1; 435/91.2; 435/91.41; 435/456; 435/472; 435/475
(58) Field of Search .................... 435/471, 472, 435/475, 235.1, 320.1, 91.2, 91.41, 456; 424/93.2, 192.1; 530/412

(56) References Cited

U.S. PATENT DOCUMENTS 5,041,379 A * 8/1991 Fraser et al. ............. 435/320.1

* cited by examiner

*Primary Examiner*—Mary E. Mosher
(74) *Attorney, Agent, or Firm*—Mathews, Collins, Shepherd & Gould, P.A.

(57) ABSTRACT

A recombinant baculovirus, which produces a recombinant polyhedra made up of a baculovirus polyhedrin (PH), a *Bacillus thuringiensis* crystal protein (CP) and jellyfish *Aequorea victoria* green fluorescent protein (GFP), is constructed by introducing a transfer vector carrying a fusion gene encoding a fusion protein in which the PH, the CP and the GFP are directly linked from N-terminal to C-terminal, in sequence, and a wild-type baculovirus into an insect cell, simultaneously, and culturing the cell. This baculovirus transfer vector pColorBtrus is constructed by synthesizing the GFP-coding DNA fragment from plasmid pGFP, the PH gene from wild-type *Autographa californica* Nucleopolyhedrovirus, and a Cry1Ac gene from plasmid pPN6.6 carrying a *Bacillus thuringiensis* Cry1Ac gene by polymerase chain reactions, and inserting first the GFP-coding DNA fragment and the PH gene in baculovirus expression vector pAcUW31 in such a way that the 5'-end of the GFP-coding DNA fragment is linked to the 3'-end of the PH gene and then, the Cry1Ac gene between the PH gene and the GFP-coding DNA fragment. The recombinant virus can kill insect pests with high pathogenicity within a short time, and is equipped with a monitoring device for infected insects, so that it can be prevented from being overused.

12 Claims, 7 Drawing Sheets

(3 of 7 Drawing Sheet(s) Filed in Color)

FIG. 5

Mock | Wt AcNPV | ColorBtrus | HD-73 toxin

RECOMBINANT BACULOVIRUS, CONSTRUCTION METHOD THEREOF AND INSECT PESTICIDAL COMPOSITION CONTAINING THE SAME

BACKGROUND OF THE INVENTION

1. Field of the Invention

The present invention relates to a novel recombinant baculovirus which exhibits quick and potent insecticidal activity, a construction method thereof and an insect pesticidal composition comprising the same.

2. Description of the Prior Art

Baculoviruses are pathogenic to insects, so that they are proliferated to kill the hosts. In addition, baculoviruses are nonpathogenic to the vertebrate and maintain their activity for a long time in fields. Owing to these advantages, as many as 20 viruses are developed as commercially available insecticides. However, baculoviruses have a limited host range and the insecticidal effects are relatively slow. These disadvantages have limited their use as control agents of insect pests.

Recently, active research has been and continues to be directed to the improvement of baculoviruses in usability as specific pest control agents. In this regard, genetic engineering technology provides a useful means therefor. In fact, a number of attempts have been made to produce the baculoviruses which are improved in killing speed, by introducing various foreign genes into the baculoviruses. The foreign genes with this purpose include those coding for *Buthus eupeus* insect toxin-1 (Carbonell et al., Gene, 73, 409–418 (1988)), *Manduca sexta* diuretic hormone (Maeda, Biochem. Biophys. Res. Commun., 165, 1177–1183 (1989)), *Heliothis virescens* juvenile hormone esterase (Hammock et al., Nature, 344, 458–461 (1990); Bonning et al., Insect Biochem. Mol. Biol., 22, 453–458 (1992)), *Pyemotes tritici* TxP-I toxin (Tomalski and Miller, nature, 352, 82–85 (1991)), *Androctonus australis* AaIT toxin (Stewart et al., Nature, 352, 85–88) and insect-specific spider toxin (Hughes et al., J. Invertebr. Pathol., 69, 112–118 (1997)). Of them, only the gene encoding scorpion toxin allowed the recombinant baculoviruses to show an increased pathogenicity. The killing speed, however, remains slow even in the baculoviruses carrying this gene.

The delta-endotoxin of *Bacillus thuringiensis* (a gram positive bacteria, hereinafter referred to as "Bt"), an insect-specific toxin which accumulates in large amounts during the sporulation of Bt, has been demonstrated as an effective means of controlling pest populations by virtue of its potent insecticidal activity and nontoxicity to humans and poultry (Feitelson et al., Bio/Technology, 10, 271–275 (1992)). As for the insecticidal mechanism of the endotoxin, it starts by enzyme cleavage. When taken in by a susceptible insect, the endotoxin is solubilized in the alkaline environment of the gut and cleaved to a smaller active protein by the action of proteases present in the gut juices. The activated protein binds to the epithelial cells of the gut, leading to disruption of the gut. While showing paralytic symptoms owing to the change in the pH of the digestive juice and humor, the susceptible insects cease to eat food and are finally put to death in 24–48 hours. For instance, the lepidoptera specific crystal protein (Cry 1), a kind of Bt endotoxin, is 130–140 kDa in total, but its toxicity is greatly enhanced if the protein is cleaved by proteases to a highly active fragment of about 60–70 kDa which corresponds to the N-terminal half of the protein (Aronson, et al., Microbiol. Rev., 50, 1–24 (1986)).

There were noticeable studies on the improvement of viral insecticidal activity by expressing the Bt endotoxin protein in baculoviruses (Bonning and Hammock, Annu. Rev. Entomol., 41, 191–210 (1996)). However, there was observed no enhancement in pathogenicity of the recombinant baculoviruses although they produce a large amount of the Bt endotoxin proteins in the blood lymphs of the insects. This results from no consideration for the insecticidal mechanism of Bt endotoxin which is fulfilled in the presence of the proteases and the epithelial cells in the gut. That is, the single Bt endotoxin protein which is expressed under the control of the promotor Ppol in the blood lymphs, is not activated as in the gut.

SUMMARY OF THE INVENTION

Bearing the activation of the baculovirus polyhedrin by protease in the alkaline environment of the insect gut in mind, the present inventors repeated thorough and intensive research with the aim of developing a novel baculovirus which can kill insect pests with high pathogenicity within a short time and finally, resulted in finding that fusion of *Bacillus thuringiensis* crystal protein with the baculovirus polyhedrin allows a significant improvement in pathogenicity and killing time.

Therefore, it is an object of the present invention to overcome the above problems encountered in prior arts and to provide a novel recombinant baculovirus which can exhibit pathogenicity within a short time.

It is another object of the present invention to provide a novel recombinant baculovirus which is equipped with a monitoring device for infected insects.

It is a further object of the present invention to provide a construction method of the recombinant baculovirus.

It is still a further object of the present invention to provide a method of constructing a transfer vector for the recombinant baculovirus.

It is still another object of the present invention to provide an insect pesticidal composition which is of potent insecticidal activity and quickness and preventive of overuse.

It is yet another object of the present invention to provide a simple purification method of proteins.

According to an aspect of the present invention, there is provided a recombinant baculovirus, which produces a recombinant polyhedra made up of a baculovirus polyhedrin (PH), a *Bacillus thuringiensis* crystal protein (CP) and jellyfish *Aequorea victoria* green fluorescent protein (GFP).

According to another aspect of the present invention, there is provided a construction method of baculovirus transfer vector pColorBtrus, comprising the steps of synthesizing a green fluorescent protein (GFP)-coding DNA fragment from plasmid pGFP by a polymerase chain reaction, synthesizing a polyhedrin (PH) gene from wild-type *Autographa californica* Nucleopolyhedrovirus by a polymerase chain reaction, inserting the green fluorescent protein-coding DNA fragment and the polyhedrin gene in baculovirus expression vector pAcUW31 in such a way that the 5'-end of the green fluorescent protein-coding DNA fragment is linked to the 3'-end of the polyhedrin gene, to yield baculovirus transfer vector pColorPol, synthesizing a Cry1Ac gene from plasmid pPN6.6 carrying a *Bacillus thuringiensis* Cry1Ac gene by a polymerase chain reaction, and inserting the Cry1Ac gene between the polyhedrin gene and the green fluorescent protein-coding DNA fragment.

According to a further object of the present invention, there is provided a method of constructing the recombinant baculovirus, comprising the steps of introducing a transfer vector carrying a fusion gene encoding a fusion protein in which a baculovirus polyhedrin, a *Bacillus thuringiensis* crystal protein and a jellyfish *Aequorea victoria* green fluorescent protein are directly linked from N-terminal to C-terminal, in sequence, and a wild-type baculovirus into an insect cell, simultaneously, and culturing the cell.

According to a further object of the present invention to provide an insecticidal composition which comprises the recombinant virus.

According to still another object of the present invention, there is provided a purification method of proteins using the transfer vector system.

BRIEF DESCRIPTION OF THE DRAWINGS

The patent or application file contains at least one photograph executed in color. Copies of this patent or patent application publication with color photographs will be provided by the Office upon requst and payment of the necessary fee.

FIG. 5 shows Western blots obtained from the recombinant polyhedra by use of an anti-Cry1Ac antibody.

FIG. 6 is a graph showing the accumulated insecticidal activity of recombinant baculovirus ColorBtrus against *P. Xylostella* larvae.

DETAILED DESCRIPTION OF THE PREFERRED EMBODIMENTS

Figure 1A:
FIGS. 1a, 1b and 1c are baculovirus transfer vector maps of pAcG, pColorPol and pColorBtrus, respectively.

Throughout the specification, the term baculoviruses mean the virions embedded in polyhedra. The polyhedra is an assembly of polyhedron-shaped polyhedrins (PH) which are expressed at the very late stage of infection in the nucleus of the infected insect. Unless specifically mentioned, the term recombinant polyhedra means the polyhedra consisting of PH-CP-GFP fusion proteins.

The PH-CP-GFP fusion protein is structured in such a way that the C-terminal of the PH protein is linked to the N-terminal of the CP whose the C-terminal is connected to the N-terminal of the GFP.

As a structural protein, the PH itself is of no pathogenicity and protects virus particles against the environment. When taken in by insects, PH is solubilized in the alkaline environment of the gut and cleaved by proteases to release virus particles.

The CF is a Bt endotoxin, examples of which include Cry1Ac, Cry1Ab, Cry I E, and protein segments containing the pathogenic natures thereof. Preferable is the Cry1Ac protein segment containing the amino acid sequence of No. 1 to No. 613. Like the PH, the CP is solubilized in the alkaline condition of the gut and cleaved to an activated pathogenic segment by proteases. For example, the pathogenic segment of Cry1Ac is the amino acid sequence of No. 27 to No. 607.

Composing the recombinant polyhedra of baculovirus, the fusion protein of the present invention, therefore, is disintegrated in the alkaline environment of the gut and by the action of proteases. That is, the fused PH is decomposed to release viruses while the CP is cleaved to the activated pathogenic segment which, then, binds to the epithelial cells of the gut, disrupting the gut. In result, the insects which take in the fusion protein of the present invention, cease to eat food and show paralytic symptoms owing to the change in the pH of the digestive juice and humor and are finally killed in 24 to 48 hours.

The GFP used in the present invention, derived from jellyfish *Aequorea victoria*, is a very stable protein which emits green light on excitation with ultraviolet. The GFP was introduced in a recombinant virus with the aim of controlling insect pests (Chao et al., Nature, 380, 396–397, 1996). In the present invention, the GFP serves to facilitate the detecting and monitoring of the recombinant baculovirus-infected larvae and their distribution in an ecosystem, thereby preventing injudicious abuse of the insecticide.

In the present invention, there was developed a novel recombinant baculovirus, ColorBtrus, which produces a recombinant polyhedra made up of the fusion protein in which an AcNPV-derived PH, a Cry1Ac protein segment of amino acid sequence No. 1 to 613, and a GFP are, in sequence, linked. The baculovirus ColorBtrus was deposited in the Korean Collection for Type Cultures, Korean Research Institute of Bioscience and Biotechnology KCTC, KRIBB, #52, Oun-dong, Yusong-ku, Taejón 305–333, Republic of Korea on Mar. 10, 1998 and received a deposition No. KCTC 0444BP.

A plausible approach to the development of the novel recombinant baculovirus, ColorBtrus, is to construct a baculovirus transfer vector carrying a fusion gene encoding the PH-CP-GFP protein. For the fusion gene, three base sequence fragments which respectively encode PH, CP and GFP, are sequentially linked. Available for the gene encoding PH are those which are derived from AcNPV, *Spodoptera exigua* NPV or *Bombix mori* NPV with preference to the PH gene of AcNPV. Examples of the CP-coding base sequence include those encoding Cry1Ac (Adang, M. J. et al., Gene, 36, 289–300 91985)), Cry1Ab, Cry1E, or protein segments containing the pathogenic natures thereof. Preferable is the base sequence corresponding to the Cry1Ac protein segment of amino acid sequence No. 1 to 613. As for the GFP-coding base sequence, it preferably contains the GFP gene derived from jellyfish *Aequorea victoria*. These base sequences may be obtained by PCR or enzymatic cleavage from vectors carrying corresponding genes or by chemical synthesis.

These sequences are sequentially linked in such a way that the 5'-end of the PH-coding base sequence and the 3'-end of the GFP-coding base sequence are the opposite ends of the resulting base sequence. This fusion sequence is inserted in a known baculovirus transfer vector, e.g., pAcUW31 (GenBank Registration No. U02452) to give a novel baculovirus transfer vector carrying a fusion gene encoding the PH-CP-GFP fusion protein.

Figure 1B:
Figure 1C:
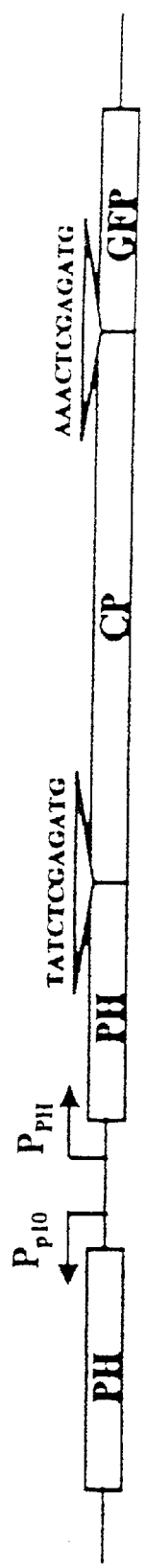

In detail, the GFP gene and the PH gene may be amplified from plasmid pGFP (Clontech) and wild-type AcNPV, respectively, by PCR. The 5'-end of the GFP gene is linked to the 3'-end of the PH gene and the linked sequence is inserted in a baculovirus expression vector PAcUW31 (Clontech) to construct a baculovirus transfer vector pColorPol (FIG. 1b). The Cry1Ac gene is amplified from plasmid pPN6.6 (obtained from Dr. Adang) by PCR and inserted between the PH gene and the GFP gene on the pColorPol to give a plasmid pColorBtrus (FIG. 1c). In the pColorBtrus, the three genes coding respectively for PH, Cry1Ac and GFP are sequentially fused. Both native polyhedrin and the fusion proteins need to be expressed in the same cell in order to stably produce the recombinant polyhedra. For this, a strategy is to create a recombinant virus with two promoters, p10 and polyhedrin gene promoters which initiate transcription of native polyhedrin and the fusion proteins, respectively, as seen in FIGS. 1*b* and 1*c*. These two independent transcription units are in opposite directions. In these vector systems, the native PH gene and the fusion genes are introduced downstream the promoter, $P_{p10}$ and $P_{PH}$, respectively.

A DNA solution of the recombinant baculovirus transfer vector thus obtained and the genomic DNA of wild-type baculovirus in 20 mM HEPES buffer is mixed with Lipofectin™ (Gibco) and allowed to stand at room temperature. Thereafter, this Lipofectin-DNA complex solution is dropwise added in a cell culture dish seeded with Sf9 cells (InVitrogen) and incubated to produce recombinant baculoviruses. For this transfection, Sf21 and Tn5 can also be used as host cells. But, preferable is Sf9. An inverted phase contrast microscope is useful to observe the polyhedra. After a predetermined time, the culture is centrifuged and the recombinant virus, ColorBtrus, is obtained from the supernatant.

The recombinant baculovirus of the present invention shows an insecticidal activity 100 times as large as, and a killing time three times as fast as those of the wild-type AcNPV. For use as an insecticide, the recombinant baculovirus may be formulated into granules, powders, liquid phase agents and aqueous solutions with preference to aqueous solutions. For example, an aqueous solution comprises $2\times10^{10}$ particles of the recombinant baculovirus, 100 g of white carbon, 100 g of sucrose, 50 g of polyvinylalcohol, 10 ml of Triton X-100 and 10 g of bentonite, added with water to a final volume of 10 liters.

The formulated insecticide composition of the present invention can be applied to the surfaces of plants, such as stone-leeks, cabbages, mulberry leaves, fruit trees, flowering plants, garden stuffs, etc, as well as to the soils in which the plants grow. In addition, the harvested vegetables can be treated with the insecticide composition during transportation or storage.

Within the targets of the insecticide of the present invention, there are included lepidopteran insects, such as *Plutella xylostella, Sopdoptera exigua,* and *Hyphantria Cunea,* etc.

A better understanding of the present invention may be obtained in light of the following examples which are set forth to illustrate, but are not to be construed to limit the present invention.

EXAMPLE I

Construction of Baculovirus Transfer Vector (1) Construction of transfer vector pAcG A GFP gene, derived from jellyfish *Aequorea victoria,* was amplified from pGFP (Clontech) by PCR using the following two primers:

[SEQ ID NO:1] 5'-AAGGATCCATGAGTAAAGGAGAAGAAC-3'

[SEQ ID NO:2] 5'-AACTGCAGCTATTTGTATAGTTCATCCATGCC-3'

The amplified gene product was digested with BamHI and PstI and inserted into the BamHI-PstI site of pBacPAK8 (Clontech) to yield a transfer vector pAcG. In this vector, the GFP gene was located downstream polyhedrin promoter ($P_{PH}$), as seen in FIG. 1*a*.

(2) Construction of transfer vector pColorPol

A PH gene was amplified from the genomic DNA of wild-type baculovirus ACNPV by PCR using the following two primers:

[SEQ ID NO:3] 5'-AGTTGCTGATATCATGG-3'

[SEQ ID NO:4] 5'-AACTCGAGATACGCCGGACCAGTG-3'

In the Sequence 3, the underlined part represents the recognition site of EcoRV.

The amplified gene product was digested with EcoRV and XhoI and inserted into the EcoRV-XhoI site of pBacPAK6 to yield a transfer vector pPol.

Separately, a GFP gene was synthesized from the pGFP by PCR using the following two primers:

[SEQ ID NO:5] 5'-AACTCGAGATGAGTAAAGGAGAAGAAC-3'

[SEQ ID NO:6] 5'-CTATTTGTATAGTTCATCCATGCC-3'

In the Sequence 5, the underlined part represents the recognition site of XhoI.

This GFP gene was digested with XhoI and SnaBI and inserted into the XhoI-SnaBI site of the plasmid pPol to yield a transfer plasmid pPolGFP. After being digested with SnaB1 and BamHI, the PH-GFP fusion gene obtained from the pPolGFP was inserted into the SnaB1-BamH1 site of an expression vector pAcUW31 (U02452) containing independent double promoters while a wild-type AcNPV PH gene was inserted into the EcoRI-BglII site of the expression vector to yield a transfer vector pColorPol. In this vector, the GFP-PH fusion gene and the AcNPV PH gene were located downstream the PH promoter ($P_{PH}$) and the p10 promoter ($P_{p10}$) as seen in FIG. 1*b*.

(3) Construction of transfer vector pColorBtrus

A Cry1Ac DNA fragment was synthesized from a plasmid pPN6.6 containing a Bt. Cry1Ac gene (Adang, M. J. et al., *Gene,* 36, 289–300 (1985)) by PCR using the following two primers:

[SEQ ID NO:7] 5'-AACTCGAGATGGATAACAATCCGAAC-3'

[SEQ ID NO:8] 5'-AACTCGAGTGTTGCAGTAACTGG-3'

In the Sequences 7 and 8, the underlined parts are the recognition site of XhoI.

This Cry1Ac DNA fragment was digested with XhoI, followed by inserting the fragment into the XhoI site of the pColorPol to yield a transfer vector pColorBtrus.

Accordingly, a PH-Cry1Ac-GFP fusion gene was located downstream the promoter $P_{PH}$ in the pColorBtrus, as seen in FIG. 1c.

EXAMPLE II

Construction of Recombinant AcNPV

1–1.5×10$^6$ Sodoptera frugiperda Sf cells (InVitrogen, Cat. No. B825-01) seeded in each of cell culture dishes were incubated at 27° C. until they attached onto the dishes. Meanwhile, a DNA solution of 1 μg of wild-type AcNPV genomic DNA (BacPAK6, Clontech, Cat. No. 6144-1) and 5 μg of the transfer vector pAcG, pColorPol or pColorBtrus DNA in 20 mM HEPES buffer, whose volume was adjusted with sterile water to 50 μl of a final volume, was added with an equivolume of Lipofectin™ (Gibco). Subsequently, the mixture was incubated at room temperature for 15 min. The cells were washed twice with 2 ml serum-free TC-100 medium (Sigma). TC-100 (1.5 ml) was added to each dish. The Lipofectin-DNA complexes were added dropwise to the medium covering the cells while gently swirling the dish. Following incubation of the cells at 27° C. for 6 hour, 1.5 ml of TC-100 supplemented with 10% FBS (Gibco BRL) and antibiotics were added to each dish and the incubation at 27° C. continued. 4 or 5 days after transfection, the supernatant was taken and centrifuged at 7,000 g for 5 min to obtain recombinant a baculovirus AcG, ColorPol or ColorBtrus. Before centrifugation, the supernatant was preferably observed with an inverted phase contrast microscope (×100) to confirm polyhedra.

EXAMPLE III

Microscopy of Recombinant Polyhedra

The recombinant baculovirus AcG, ColorPol or ColorBtrus was seeded at a population of 2.0×10$^6$ per 60 mm×15 mm plate and allowed to stand for 1 hour before infection to Sf9 cells. In regard to infection, about 5 viruses per Sf9 cell were preferred. To characterize the expression of the recombinant polyhedrin or the fusion proteins, the cells infected with the recombinant baculovirus were observed at 4 days postinfection by a light microscope and a fluorescent microscope (Axiophot Universal Microscope, Zeiss, ×1,000). As a control, a wild-type baculovirus AcNPV (Clontech, Cat. No. K1601-D) was used.

Figures 2A, 2B, 2C, 2D, 2E, 2F, 2G, 2H:
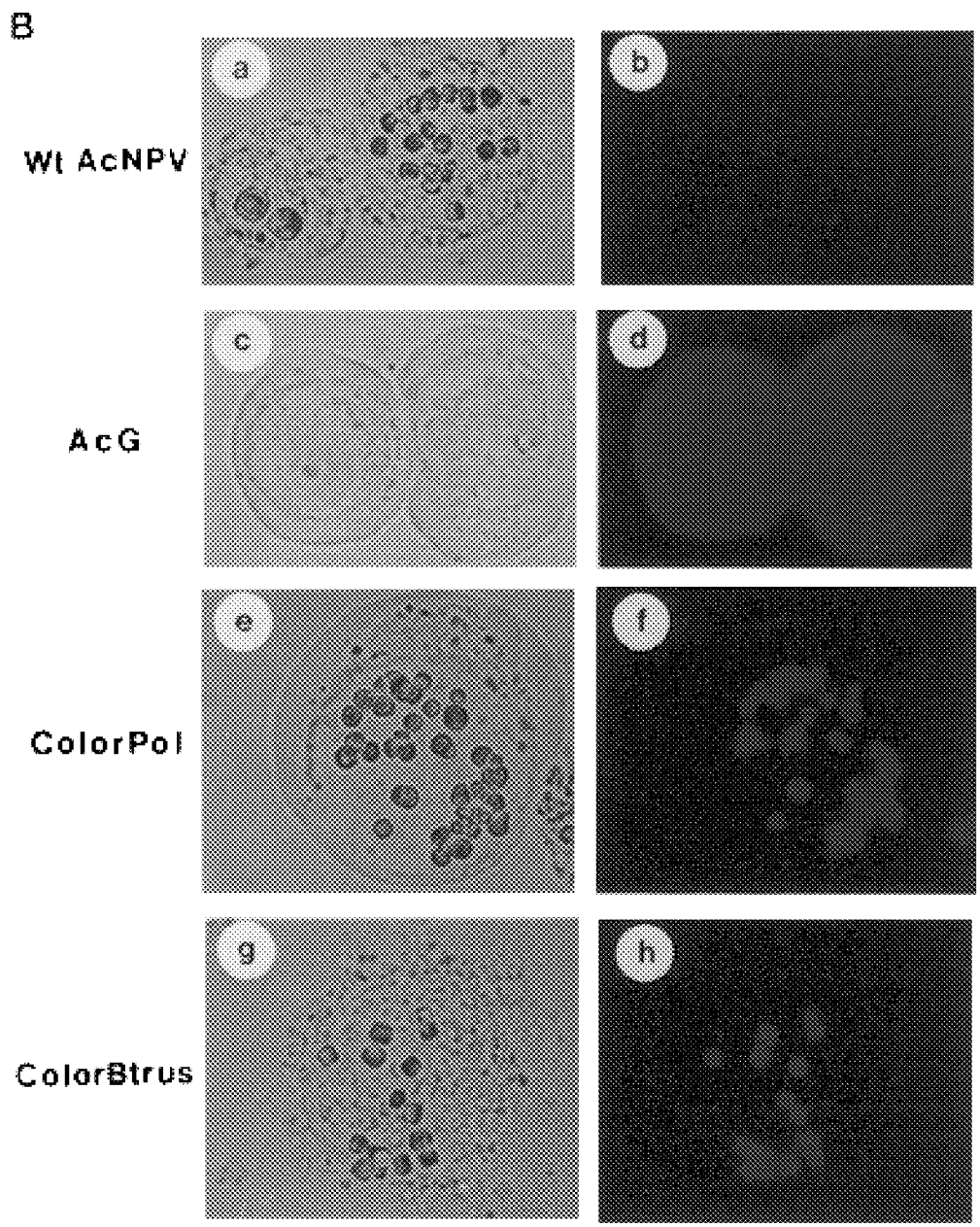
FIGS. 2a and 2b are respectively light and fluorescent microphotographs, showing Sf9 cells infected with control (wild-type) AcNPV.
FIGS. 2c and 2d are respectively light and fluorescent microphotographs, showing sf9 cells infected with recombinant baculovirus AcG.
FIGS. 2e and 2f are respectively light and fluorescent microphotographs, showing sf9 cells infected with recombinant baculovirus ColorPol.
FIGS. 2g and 2h are respectively light and fluorescent microphotographs, showing sf9 cells infected with recombinant baculovirus ColorBtrus.

The results are shown in FIGS. 2a to 2h. FIGS. 2a and 2b are respectively a light microphotograph and a fluorescent microphotograph for the Sf9 cells infected with wild-type AcNPV, FIGS. 2c and 2d for the Sf9 cells infected with AcG, FIGS. 2e and 2f for the Sf9 cells infected with ColorPol, and FIGS. 2g and 2h for the Sf9 cells infected with ColorBtrus.

As seen in FIGS. 2e to 2h, the fusion proteins of ColorPol and ColorBtrus have normal polyhedra shapes, emitting green light under ultraviolet light. Thus, this microscopy of the cells infected with the recombinant baculovirus ColorPol and ColorBtrus revealed that GFP with fluorescence activity was fused in the polyhedra. In contrast, the polyhedra produced from the wild-type baculovirus AcNPV had a normal appearance, but did not emit green light under ultraviolet light. For AcG, the bright glow of the GFP produced clearly appeared in the whole cells.

EXAMPLE IV

Western Blot Analysis of Recombinant Polyhedra

Sf9 cells were infected with the recombinant baculoviruses AcG, ColorPol and ColorBtrus in the same manner as that of Example III. After incubation at 27° C., the cells were harvested at 3 days postinfection by centrifugation at 4,000×g for 5 min. After being washed with PBS and mixed with 5×sample buffer [0.6 ml 1 M Tris-HCl (pH 6.8), 5 ml 50% glycerol, 2 ml 10% SDS, 0.5 ml β-mercaptoethanol, 1 ml 1% bromophenol blue, 0.9 ml H$_2$O), the cells were water-boiled at 100° C. for 5 min, allowed to stand at room temperature for a while and then, clarified by centrifugation at 7,000×g for 5 min. The supernatants of the cell lysates were electrophoresed on a 10% polyacrylamide separation gel with a 3% stacking gel containing SDS. The proteins run on the gel were transferred to nitrocellulose membrane. After blotting, the membrane was bound with anti-GFP antibody (Clontech, Cat. No. 8363-2), anti-AcNPV PH antibody (possessed in the Laboratory of Insect Pathology and Genetic Engineering Division of Applied Biology and Chemistry, Seoul National University) Or anti-Bt Cry1Ac antibody (possessed in the Laboratory of Insect Pathology and Genetic Engineering Division of Applied Biology and Chemistry, Seoul National University) and then, incubated with goat anti-rabbit IgG alkaline phosphatase conjugate (Sigma) at room temperature.

Figures 3A, 3B, 3C:
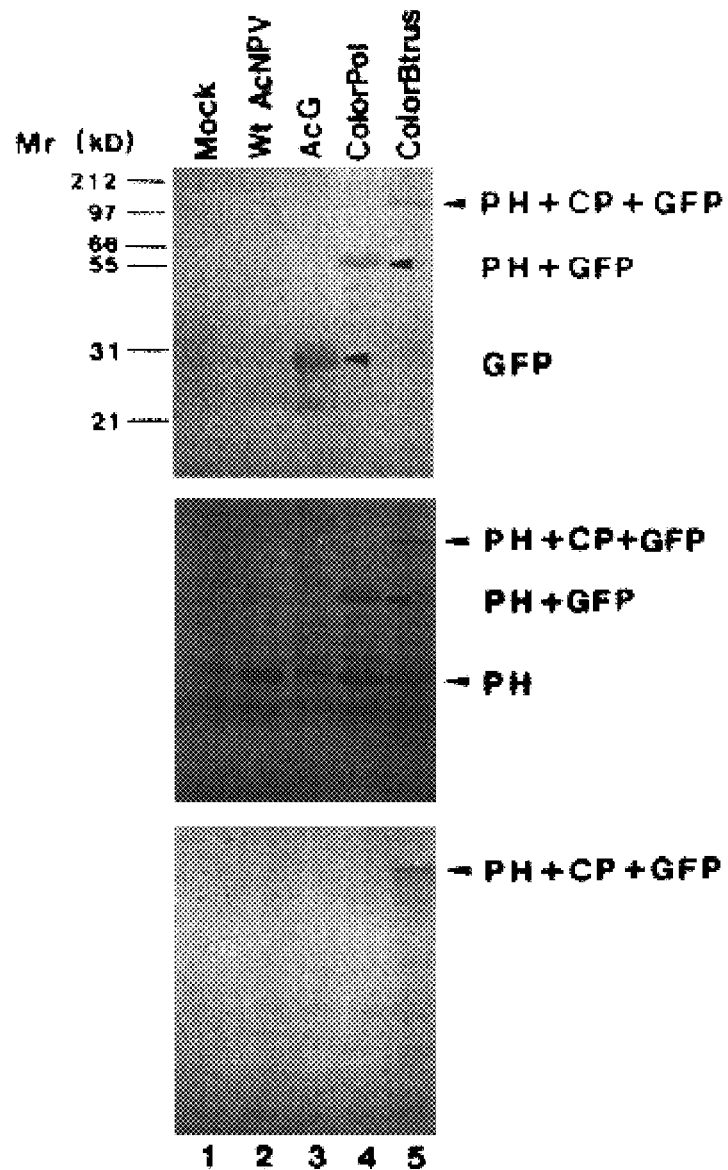
FIGS. 3a, 3b and 3c show the western blots obtained from the recombinant polyhedra by use of anti-GFP antibody, anti-PH antibody and anti-Cry1Ac antibody, respectively.

The western blots obtained by use of an anti-GFP antibody, an anti-PH antibody and an anti-Cry1Ac antibody are given as shown in FIGS. 3a, 3b and 3c, respectively. As demonstrated from the figures, the polyhedras produced from the recombinant baculoviruses ColorPol and ColorBtrus, were composed of a PH-GFP fusion protein 60 kDa in molecular weight and a PH-Cry1Ac-GFP, respectively.

EXAMPLE V

Electromicroscopy of Immunogold-labeled Recombinant Polyhedra

Samples were prepared by ultracentrifuging the same recombinant baculoviruses ColorBtrus and wild-type AcNPV cultures as in Example III in a gradient sucrose ranging from 40 to 65% and isolating the AcNPV polyhedra and the ColorBtrus polyhedra at the 56% region. These samples were fixed in a 0.1 M PBS (pH 7.5) containing 1% (w/v) para-formaldehyde, rinsed with 0.1 M glycine (pH 7.5), dehydrated and then, embedded in Lowicryl K4M (polysciences). Ultrathin sections of the embedded polyhedras were treated with an anti-GFP antibody, an anti-Cry1Ac antibody and an anti-PH antibody on nickel grids. These sections were exposed to a secondary antibody, such as colloidal gold-conjugated goat anti-rabbit antibody (Biocell), and stained with 0.2% lead citrate and 2% uranyl acetate before being observed with a transmission electron microscope (Hitachi M-600).

Figure 4A:
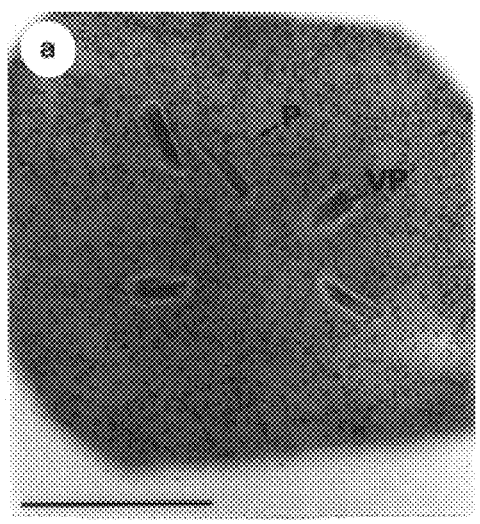
FIGS. 4a and 4b are transmission electron microphotographs showing the immunogold-labeled recombinant polyhedra of wild-type AcNPV and the recombinant ColorBtrus polyhedra, respectively.
Figure 4B:
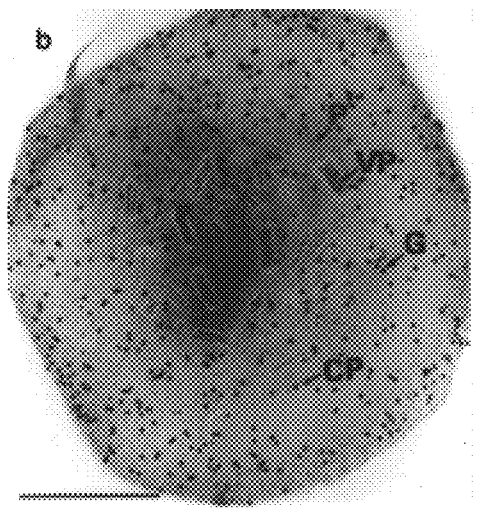

Referring to FIG. 4, there are transmission electron microphotographs showing the immunogold-labeled recombinant polyhedra. The wild-type AcNPV polyhedra is shown in FIG. 4a and the recombinant ColorBtrus polyhedra in FIG. 4b. In the photographs, GFP, Cry1Ac and PH are discriminated by the gold particles with a diameter of 30 nm, 20 nm and 10 nm, respectively. As seen, gold particles with anti-PH, Cry1Ac and GFP antibodies are concurrently observed in the recombinant polyhedra of ColorBtrus while only gold particles with an anti-PH antibody are shown in FIG. 4a. This transmission electron microscopy, therefore, revealed that the recombinant polyhedra of ColorBtrus was a fusion protein of PH, Cry1Ac and GFP.

EXAMPLE VI

Western Blot Analysis of Recombinant Polyhedra Treated with Silkworm Gut Juice The gut juices vomited from the 5th instar silkworm shocked with an electric current, were added to equivolumes of a wild-type AcNPV polyhedra, the recombinant ColorBtrus polyhedra and a Bt Cry1Ac protein and allowed to stand at room temperature for 5 min. These samples were subjected to 10% SDS-PAGE and Western blot analysis using an anti-Bt Cry1Ac antibody, in the same manner as in Example IV. Upon mock infection, water was used.

Figures 5, 6:
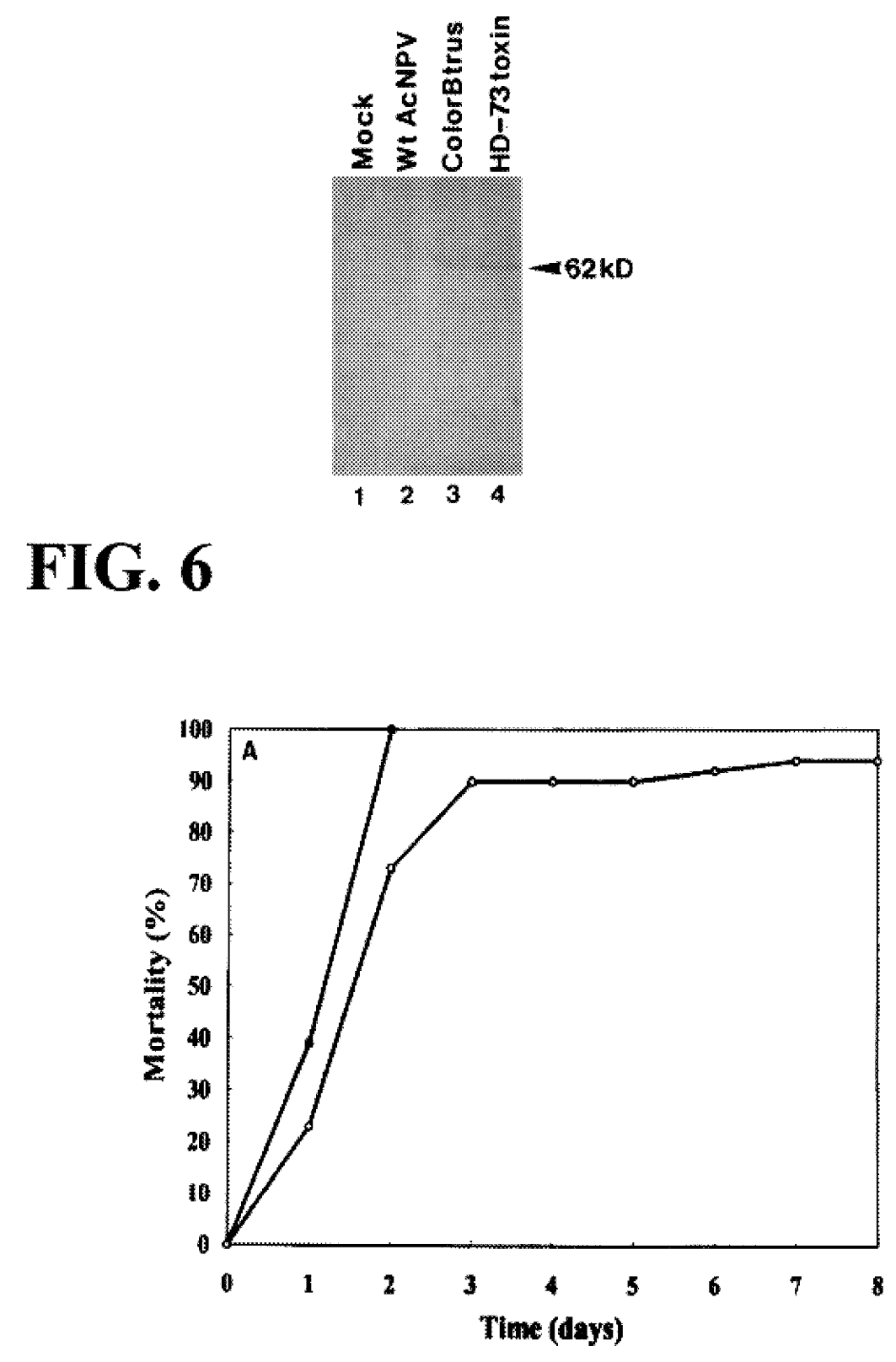

The Western blots are shown in FIG. 5. In the ColorBtrus lane, a band of about 65 kDa was detected which is identical to the cleaved, active protein of Cry1Ac. Thus, the data demonstrate that the recombinant polyhedra of ColorBtrus taken by insects are immediately solubilized in the alkaline environment of the gut juice and cleaved to the activated toxin by the action of the proteases present therein.

EXAMPLE VII

Insecticidal Bioassay of Recombinant Virus

The toxicity of the recombinant virus ColorBtrus was determined against the Diamondback moth, *Plutella xylostella* with a control of wild-type AcNPV. To determine the median lethal dose ($LD_{50}$), fifty second instar larvae were fed with eight 2-fold series diluted virus stocks (5120, 1280, 640, 320, 160, 80, 40 and 20 polyhedra per larva) on Chinese cabbage leaves. Larvae that consumed the dose in 24 hr were transferred to fresh leaves of Chinese cabbage and examined daily. The mortality was scored for a determined time for the determination of $LD_{50}$. This procedure was repeated three times.

In order to determine the median survival time $ST_{50}$, fifty second-instar larvae each were fed with a virus suspension (1500 polyhedra per larva) on Chinese cabbage leaves.

The results are given in Table 1, below.

TABLE 1

| Virus | $LD_{50}$ (No. polyhedra/larva) | $ST_{50}$ (hr) |
| --- | --- | --- |
| wt AcNPV | 3,000 | 153.6 |
| ColorBtrus | 29.6 | 31.8 |

The improved insecticidal activity of the recombinant polyhedra of ColorBtrus was demonstrated by reduction in both medial lethal dose ($LD_{50}$) and median survival time ($ST_{50}$). For *P. Xylostella* larvae, the recombinant virus ColorBtrus shows 100-fold increased insecticidal activity and 5-fold decreased killing time compared with the wild-type AcNPV virus. Therefore, the recombinant virus of the present invention, even though used at a significantly small amount, is able to kill insect pests within a short time.

With reference to FIG. 6, there is shown the accumulated insecticidal activity of the recombinant baculovirus ColorBtrus against *P. Xylostella* larvae. When *P. xylostella* was fed at a dose of 5120 (closed circle ●) and 1280 (open circle ○) recombinant polyhedra per larva, the mortality reached approximately up to 100% and 90%, respectively, in three days. In the latter case, the number of dead larvae started to increase again at the sixth day from the treatment, and the mortality reached 94% finally.

Figures 7A, 7B:
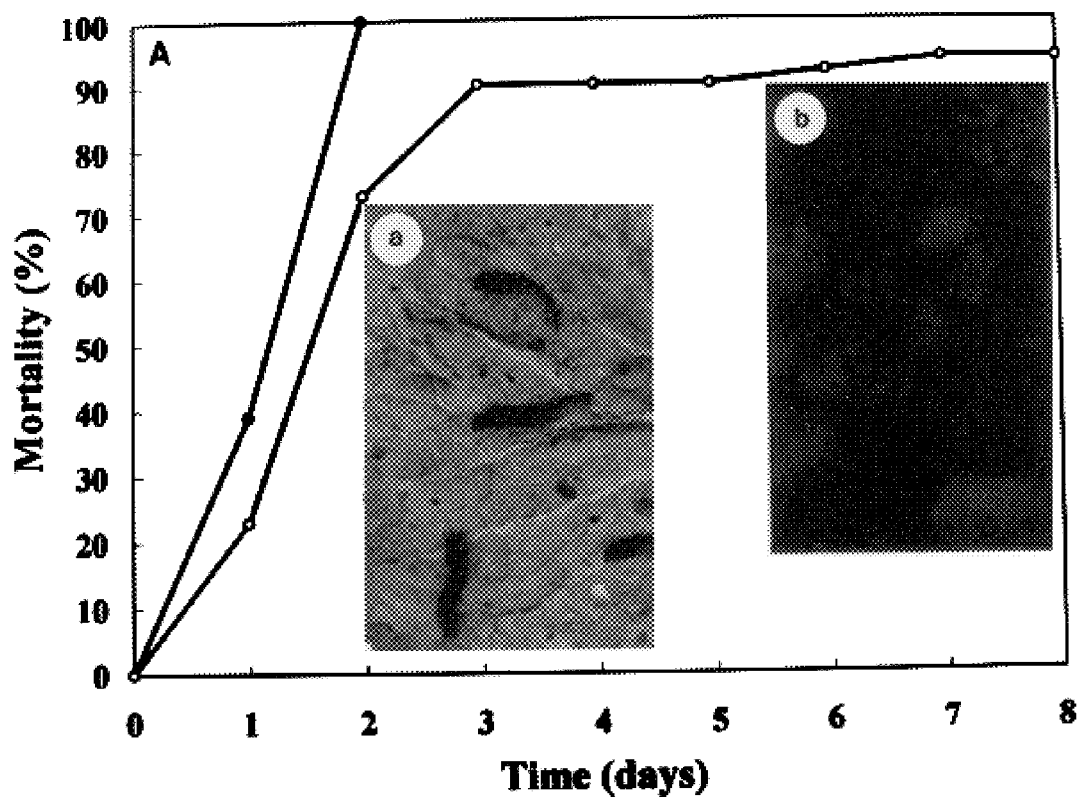
FIG. 7a is a photograph showing *P. xylostella* larvae which were infected with the recombinant polyhedra of ColorBtrus three days earlier.
FIG. 7b is a fluorescent microphotograph showing the fat body from the dead larvae which was infected with ColorBtrus six days earlier.

FIG. 7a shows *P. xylostella* larvae which were infected with the recombinant polyhedra of ColorBtrus three days earlier and FIG. 7b is a fluorescent microphotograph showing the fat body from the dead larvae which was infected with ColorBtrus six days earlier. The larvae which were killed at three days postinfection, exhibited a typical symptom due to Bt Cry1Ac (a) and the production of the recombinant polyhedra by the ColorBtrus was confirmed from the fat body from the dead larvae infected with ColorBtrus at 6 days postinfection (b). These data reveal that the recombinant baculovirus ColorBtrus has a killing power endowed from the crystal protein until 3 days postinfection while killing the larvae by viral replication from 6 days postinfection.

Figures 8A, 8B:
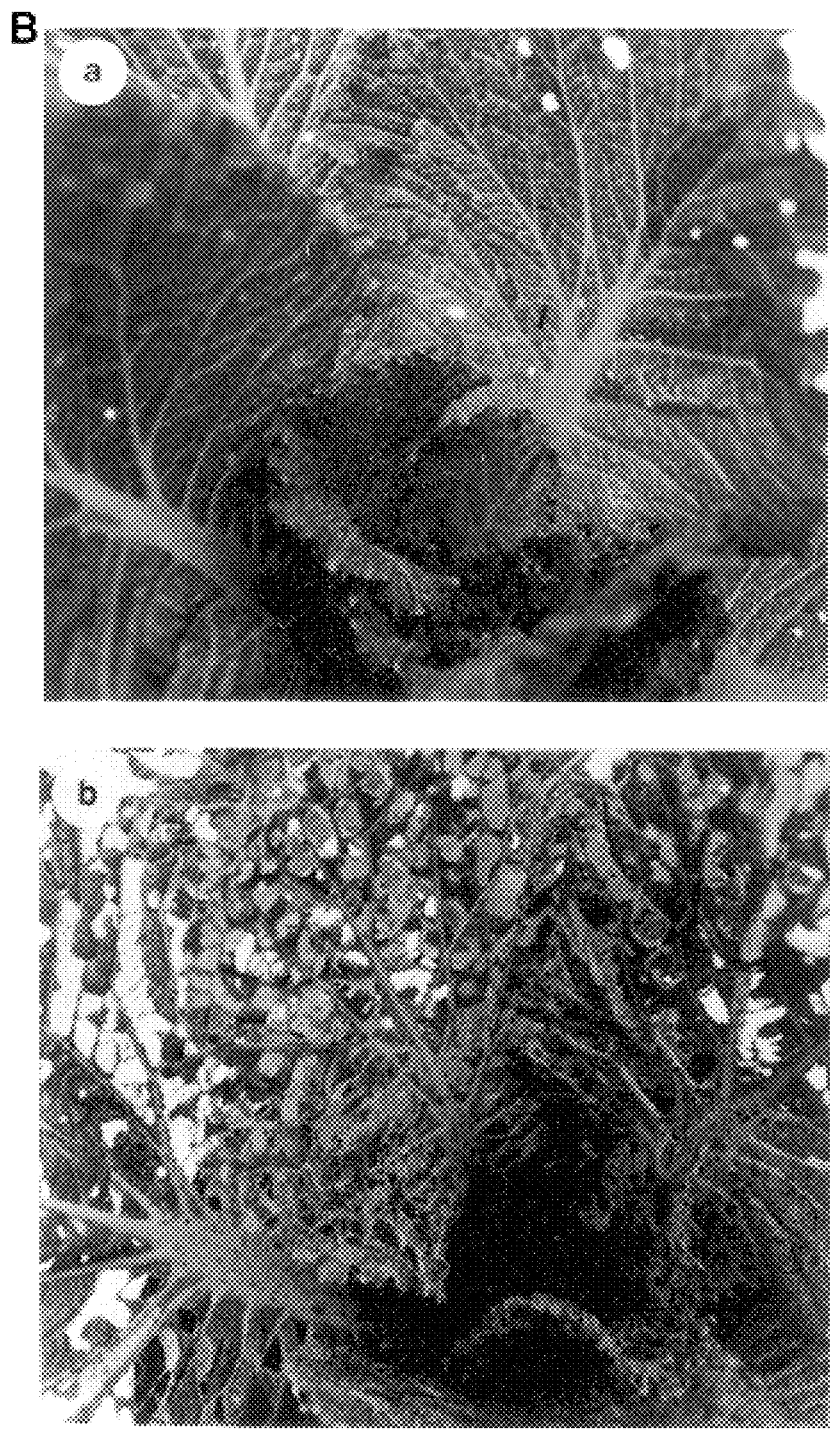
FIGS. 8a and 8b are microphotographs showing a reduction in feeding damage by ColorBtrus-infected *P. xylostella* larvae on Chinese cabbage leaves which the polyhedra of ColorBtrus and wild-type AcNPV were treated, respectively.

Referring to FIG. 8, there is shown a reduction in feeding damage by ColorBtrus-infected *P. xylostella* larvae. The polyhedra of ColorBtrus (FIG. 8a) and of wild-type AcNPV (FIG. 8b) were treated on Chinese cabbage leaves. As seen, *P. xylostella* larvae treated with the recombinant polyhedra of ColorBtrus caused much less damage to the leaves than did the larvae infected with wild-type AcNPV.

According to another aspect of the present invention, foreign proteins can be introduced to the polyhedra of wild type AcNPV, thereby constructing a novel baculovirus expression vector system which expresses many foreign proteins and facilitates their isolation, as apparent in the recombinant baculovirus ColorBtrus. Because almost all of the proteins which are expressed in conventional expression vectors are present in soluble forms, they are difficult to purify and require expensive apparatuses in the purification. In contrast, the novel baculovirus expression system carrying the polyhedra gene expresses the introduced foreign proteins in a form convenient to purify, for example, only by centrifugation. Thus, a significant economical profit can be obtained in terms of time and cost. Examples of the proteins which can be expressed by the baculovirus expression vector system of the present invention, include veterinary medicines such as interferon for cats or dogs, human medicines such as anticancer agents, insulin and interferon, antibacterial agents, antibiotics, etc.

In addition, the recombinant polyhedra of the present invention can be applied for vaccine development. If a gene encoding foreign protein for use as a vaccine is fused to the gene encoding the polyhedrin protein in the baculovirus expression vector system, the foreign protein can be produced in a crystalline form along with the polyhedrin protein which is harmless to the body, so that the protein can maintain its vaccinal function without the aid of an adjuvant.

As described hereinbefore, the recombinant baculovirus ColorBtrus of the present invention expresses polyhedra made up of a PH-CP-GFP fusion protein the CP moiety of which is solubilized in the alkaline environment of an insect's gut juice and cleaved to an active form by proteases while the virions are released. Thus, a baculovirus insecticide of the recombinant polyhedra of ColorBtrus exerts the double action mode of Bt crystal protein and viral replication of AcNPV on insects, improving its pathogenicity and host range. Moreover, because the recombinant polyhedra emits green fluorescence under UV light, it can be applied for monitoring and/or detecting infected insects in fields. In addition, this watching device can prevent the insecticide from being overused.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A recombinant baculovirus comprising a genome wherein the genome comprises two independent transcription units:
   wherein the first transcription unit comprises a nucleic acid sequence encoding a functional polyhedrin protein capable of forming a paracrystalline lattice around the viral particle operably linked to promoter; and,
   wherein the second transcription unit transcribes a fusion gene wherein the fusion gene comprises a nucleic acid sequence encoding a polyhedrin, a gfp nucleic acid sequence encoding a green fluorescent protein of a jellyfish *Aequorea victoria* and nucleic acid sequence encoding a *Bacillus thuringiensis* crystal protein, or fragment thereof, having insecticidal activity and in which the nucleic acid sequences are sequentially linked and are operably linked to a polyhedrin promoter so that infectious occlusion bodies with the viral particle produced from said baculovirus contains a fusion gene product, wherein the fusion gene product encodes a fusion protein wherein the baculovirus polyhedron protein, *Bacillus thuringiensis* crystal protein and jellyfish *Aequorea victoria* green fluorescent protein are sequentially linked from N-terminal to C-terminal.

2. A recombinant baculovirus as set forth in claim 1, wherein said baculovirus polyhedrin is derived from *Autographa californica* Nucleopolyhedrovirus and said *Bacillus thuringiensis* crystal protein is a Cry1Ac protein segment containing the amino acid sequence of amino acids 1–613.

3. A recombinant baculovirus as set forth in claim 1 wherein said promoter is a P10 promoter.

4. An insecticidal composition comprising the recombinant baculovirus of claim 1.

5. A method of combating insect pests at a locus comprising treating the pests or locus with the recombinant baculovirus of claim 1.

6. A method of monitoring and/or detecting insects infected with the recombinant baculovirus of claim 1 by observing green fluorescence under UV light emitted by the recombinant polyhedra fusion proteins.

7. A baculovirus transfer vector, carrying a gene encoding a fusion protein in which a baculovirus polyhedrin, a *Bacillus thuringiensis* crystal protein and a jellyfish *Aequorea victoria* green fluorescent protein are directly linked from N-terminal to C-terminal, in sequence.

8. A transfer vector as set forth in claim 7 which is the plasmid pColorBtrus.

9. A method of making DNA coding a fusion protein in which a baculovirus polyhedron sequence, a *Bacillus thuringiensis* crystal protein sequence and a jellyfish *Aequorea victoria* green fluorescent protein sequence are directly linked from N-terminal to C-terminal in sequence comprising the steps of:

synthesizing a green fluorescent protein-coding DNA fragment from plasmid pGFP by a polymerase chain reaction;

synthesizing a polyhedrin gene from wild-type *Autographa californica* Nucleopolyhedrovirus by a polymerase chain reaction;

inserting the green fluorescent protein-coding DNA fragment and the polyhedrin gene in the baculovirus expression vector in such a way that the 5'-end of the green fluorecent protein-coding DNA fragment is linked to the 3'-end of the polyhedrin gene, to yield a baculovirus transfer vector;

synthesizing a Cry1Ac gene from a plasmid carrying a *Bacillus thuringiensis* Cry1Ac gene by a polymerase chain reaction; and inserting the Cry1Ac gene between the polyhedrin gene and the green fluorescent protein-coding DNA fragment.

10. A recombinant baculovirus comprising a genome wherein the genome comprises two independent transcription units of a polyhedrin gene wherein the first transcription unit expresses functional polyhedrin protein capable of forming a paracrystalline lattice around a viral particle and wherein the second transcription unit comprises a fusion gene in which a polyhedrin gene and a heterologous gene which expresses a desired foreign protein with a specific function are sequentially linked and are under the same control of a promoter so that infectious occlusion bodies with the viral particle produced from said baculovirus contains a fusion gene product, wherein the fusion gene product expresses a fusion protein wherein the C-terminal of the polyhedrin protein is linked to the N-terminal of the foreign protein.

11. A recombinant baculovirus as set forth in claim 10 wherein said promoter is a p10 or polyhedrin promoter.

12. A method for producing baculovirus comprising the steps of:

infecting an insect cell with a recombinant baculovirus as in claims 1 or 10; and culturing the cell under conditions suitable for the production of progeny particles.

* * * * *

SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 1
aaggatccat gagtaaagga gaagaac                                           27

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 2
aactgcagct atttgtatag ttcatccatg cc                                     32

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 3
agttgctgat atcatgg                                                      17

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
aactcgagat acgccggacc agtg                                              24

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 5
aactcgagat gagtaaagga gaagaac                                           27

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 6
ctatttgtat agttcatcca tgcc                                              24

<210> SEQ ID NO 7
<211> LENGTH: 26

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 7
aactcgagat ggataacaat ccgaac                                      26

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 8
aactcgagtg ttgcagtaac tgg                                         23
```